(12) United States Patent
Schiller et al.

(10) Patent No.: US 9,480,801 B2
(45) Date of Patent: Nov. 1, 2016

(54) TAMPER EVIDENT TIP CAP AND SYRINGE

(75) Inventors: Eric Schiller, Westfield, NJ (US); Frederic Perot, Saint Paul de Varces (FR)

(73) Assignee: Becton Dickinson France, Le Pont-de-Claix (FR)

( * ) Notice: Subject to any disclaimer, the term of this patent is extended or adjusted under 35 U.S.C. 154(b) by 1010 days.

(21) Appl. No.: 12/859,830

(22) Filed: Aug. 20, 2010

(65) Prior Publication Data

US 2011/0046550 A1    Feb. 24, 2011

Related U.S. Application Data

(60) Provisional application No. 61/235,822, filed on Aug. 21, 2009.

(51) Int. Cl.
| | |
|---|---|
| *A61M 5/00* | (2006.01) |
| *A61M 5/50* | (2006.01) |
| *A61M 5/28* | (2006.01) |
| *A61M 5/31* | (2006.01) |

(52) U.S. Cl.
CPC ............ *A61M 5/5086* (2013.01); *A61M 5/28* (2013.01); *A61M 5/3134* (2013.01); *A61M 2205/583* (2013.01)

(58) Field of Classification Search
CPC .......... A61M 2205/583; A61M 5/28; A61M 5/3134; A61M 5/5086
USPC ......................................... 604/111
See application file for complete search history.

(56) References Cited

U.S. PATENT DOCUMENTS

| | | |
|---|---|---|
| 3,364,890 A | 1/1968 | Andersen |
| 3,978,859 A | 9/1976 | Goodenough et al. |
| 4,148,316 A | 4/1979 | Xanthopoulos |
| 4,390,016 A | 6/1983 | Riess |
| 4,418,827 A | 12/1983 | Butterfield |
| 4,430,077 A | 2/1984 | Mittleman et al. |
| 4,471,879 A | 9/1984 | Connor et al. |
| 4,571,242 A | 2/1986 | Klein et al. |
| 4,667,837 A | 5/1987 | Vitello et al. |
| 4,832,695 A | 5/1989 | Rosenberg et al. |
| 5,135,496 A | 8/1992 | Vetter et al. |
| 5,230,429 A | 7/1993 | Etheredge, III |
| 5,328,474 A | 7/1994 | Raines |

(Continued)

FOREIGN PATENT DOCUMENTS

| | | |
|---|---|---|
| WO | 2007/121915 A1 | 11/2007 |
| WO | 2010/091133 A2 | 8/2010 |
| WO | WO 2010091133 A2 * | 8/2010 |

*Primary Examiner* — Jason Flick
(74) *Attorney, Agent, or Firm* — The Webb Law Firm

(57) ABSTRACT

A pre-filled syringe assembly having a tamper evident tip cap is provided for indicating if the contents of the syringe assembly have been compromised. The syringe barrel has an interior chamber which defines a pressure therein and is sealed at the proximal and distal ends by a first and second seal, respectively, to maintain this pressure. The second seal is formed of a deformable material and a tip cap is located about the second seal and distal end of the syringe barrel. This tip cap includes a viewable indicator representing a change in state of the syringe contents. The indicator has a portion positioned in contact with the second seal such that the first distinguishing feature is viewable through a portion of the cap. Tampering of the contents within the interior chamber causes a change in pressure and movement of the indicator indicating tampering of the syringe assembly.

25 Claims, 7 Drawing Sheets

(56) References Cited

U.S. PATENT DOCUMENTS

| | | |
|---|---|---|
| 5,334,144 A | 8/1994 | Alchas et al. |
| 5,785,691 A | 7/1998 | Vetter et al. |
| 5,950,819 A | 9/1999 | Sellars |
| 6,068,614 A | 5/2000 | Kimber et al. |
| 6,126,640 A * | 10/2000 | Tucker et al. ............ 604/187 |
| 6,190,364 B1 * | 2/2001 | Imbert ..................... 604/256 |
| 6,193,688 B1 | 2/2001 | Balestracci et al. |
| 6,344,031 B1 | 2/2002 | Novacek et al. |
| 6,485,460 B2 | 11/2002 | Eakins et al. |
| 6,491,665 B1 | 12/2002 | Vetter et al. |
| 6,520,935 B1 | 2/2003 | Jansen et al. |
| 6,585,691 B1 | 7/2003 | Vitello |
| 6,821,268 B2 | 11/2004 | Balestracci |
| 6,846,303 B2 | 1/2005 | Eakins et al. |
| 6,878,131 B2 | 4/2005 | Novacek et al. |
| 6,921,383 B2 | 7/2005 | Vitello |
| 7,041,087 B2 | 5/2006 | Henderson et al. |
| 7,374,555 B2 | 5/2008 | Heinz et al. |
| 7,632,244 B2 | 12/2009 | Buehler et al. |
| 7,645,267 B2 | 1/2010 | Vetter et al. |
| 2004/0133169 A1 | 7/2004 | Heinz et al. |
| 2004/0225258 A1 | 11/2004 | Balestracci |
| 2004/0254531 A1 | 12/2004 | Carr et al. |
| 2005/0192534 A1 | 9/2005 | Wolbring et al. |
| 2007/0106243 A1 | 5/2007 | Faries, Jr. et al. |
| 2007/0250017 A1 | 10/2007 | Carred et al. |
| 2008/0097310 A1 * | 4/2008 | Buehler et al. ............ 604/111 |
| 2008/0171981 A1 | 7/2008 | Khan et al. |
| 2009/0082737 A1 | 3/2009 | Bobst et al. |
| 2009/0149817 A1 | 6/2009 | Frezza |

\* cited by examiner

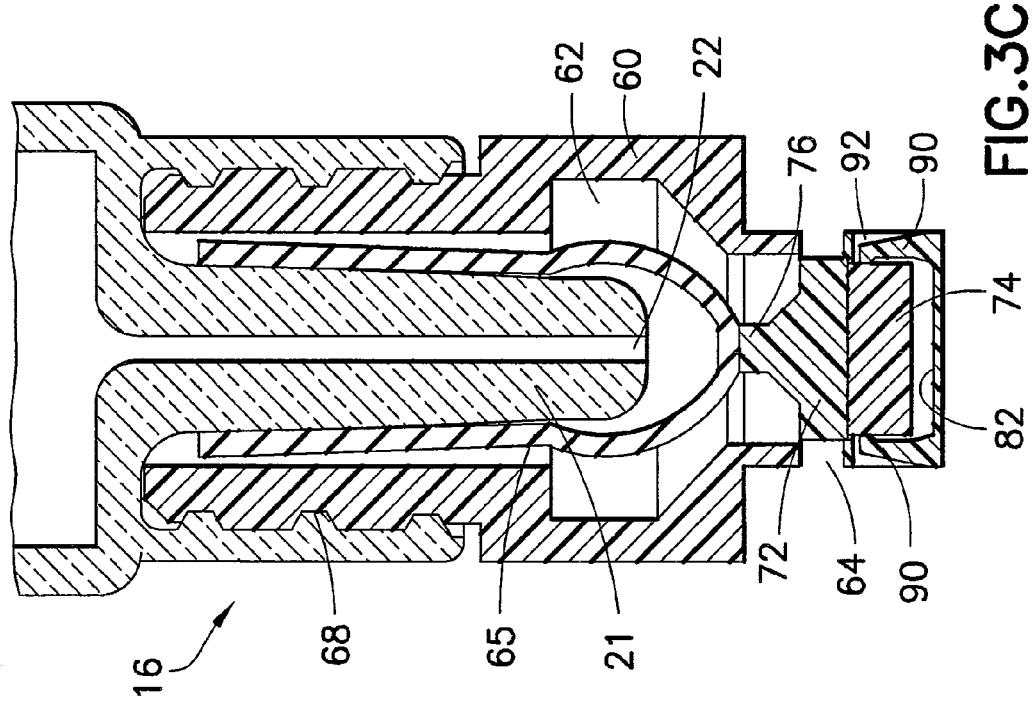
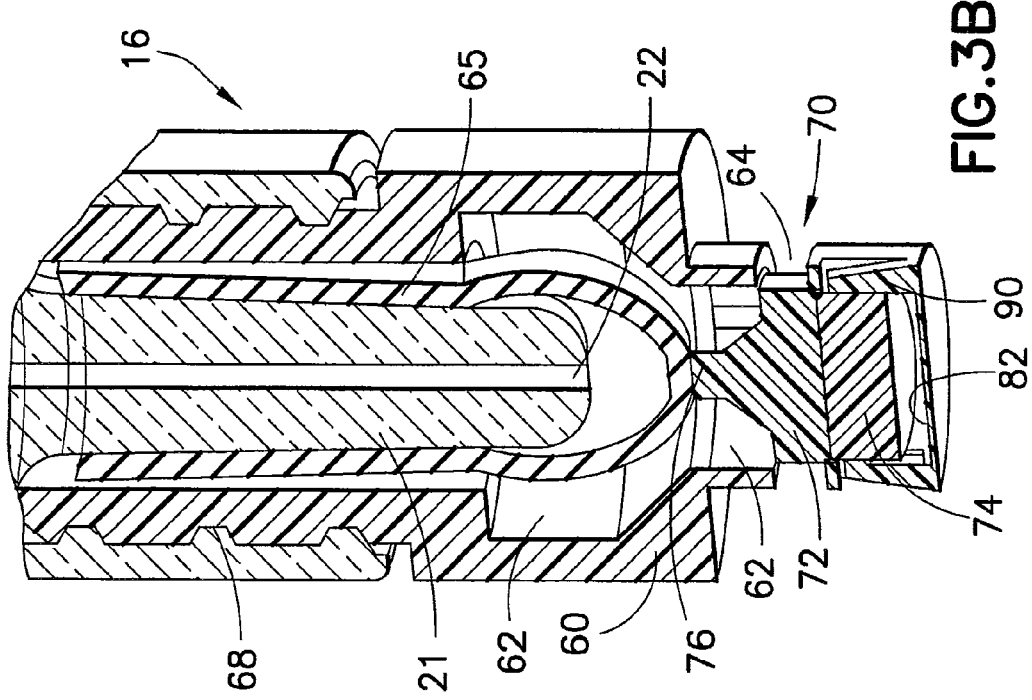
FIG.3B
FIG.3C

TAMPER EVIDENT TIP CAP AND SYRINGE

CROSS REFERENCE TO RELATED APPLICATIONS

This application claims benefit of U.S. Provisional Patent Application No. 61/235,822 entitled "Tamper Evident Tip Cap and Syringe" filed Aug. 21, 2009, which is hereby incorporated by reference in its entirety.

BACKGROUND OF THE INVENTION

1. Field of the Invention

The present invention is directed to a pre-filled syringe assembly adapted for dispensing and delivery of a fluid. More particularly, the present invention is directed to a pre-filled syringe assembly having a tamper evident tip cap providing an indication if the contents of the syringe assembly have been compromised.

2. Description of Related Art

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. Even though measures, such as controlled storage, are taken to ensure that the contents of these syringes remain intact, the risk still remains that the syringe contents can be tampered with and/or stolen and replaced with a saline solution. One technique for preventing tampering is the use of a snap cap for the tip cap that makes a snapping noise when removed from the syringe assembly. U.S. Pat. No. 4,667,837 to Vitello et al. discloses a tamper proof cap for a pre-filled syringe comprising a top member concentrically disposed in a generally cylindrical sleeve member and connected by frangible elements to the sleeve member. U.S. Pat. No. 7,041,087 to Henderson et al. discloses an outer cap for a pre-filled syringe that is covered with a cylindrical cover cap which connects with the top wall of a holding member through a frangible portion. The cylindrical cover cap may be broken from the top wall of the holding member for tampering prevention/tamper-proof evidence. One drawback to this type of system is that the contents of the syringe can be heated and the cap reapplied to "reset" it to its previously deformed state, or the user tampering with the device can use an additional syringe to create a vacuum inside the "tampered" syringe and reset the snap cap. Then, it appears as if the syringe has not been tampered with. In these tamper resistant systems, a shrink wrap band is required to show that the cap has not been altered. It is desirable to produce pre-filled syringes having a readily viewable, non-reversible tamper indicator that ensures the integrity of the syringe contents.

SUMMARY OF THE INVENTION

According to one aspect, the invention is directed to a tamper evident pre-filled syringe assembly comprising a syringe barrel defining an interior chamber, a proximal end, and a distal end terminating in a tip having an opening extending therethrough, the syringe barrel defining a pressure contained within the interior chamber and an indicator associated with the syringe assembly. The indicator is configured for changing state upon a change in the pressure within the interior chamber to indicate tampering of contents within the syringe assembly. The syringe assembly can further include a first seal for sealing the interior chamber and a second seal for sealing the opening extending through the tip of the distal end of the syringe barrel. According to one embodiment, the plunger assembly can include a plunger head wherein the plunger head extends within the syringe barrel and comprises the first seal. The second seal can be positioned about the distal end of the syringe barrel and is formed from a deformable material. Tampering of contents within the syringe barrel causes a change in the pressure within the interior chamber resulting in a deformation of the second seal. The indicator can be associated with the second seal such that deformation of the second seal results in movement of the indicator.

According to one embodiment, the pressure defined by the interior chamber can be a positive pressure, wherein tampering with the syringe contents reduces the pressure within the interior chamber resulting in deformation of the second seal and movement of the indicator toward a proximal end of the syringe assembly.

According to another embodiment, the pressure defined by the interior chamber can be a negative pressure, wherein tampering with the syringe contents results in an increase of pressure within the syringe barrel resulting in deformation of the second seal and movement of the indicator toward a distal end of the syringe assembly.

The change in state of the indicator can comprise a visual change. For example, this visual change can be a color change, an indicia change, or any other visually distinguishable contrast.

The syringe assembly can further include a tip cap located about the distal end of the syringe barrel. The tip cap can contain at least a portion of the indicator therein and at least one viewing portion for viewing the change of state of the indicator. The viewing portion can comprise a cut-out portion in a wall of the tip cap. Alternatively, the viewing portion can comprise a transparent portion in the tip cap. The tip cap can be threadedly engaged with the distal end of the syringe barrel. A holding member can be provided for cooperating with the indicator and for preventing the indicator from returning to an original pre-tampered state. For example, this holding member can comprise flexible fingers or a washer.

According to another aspect, the invention is directed to a tamper evident pre-filled syringe assembly comprising a syringe barrel defining an interior chamber, a proximal end, and a distal end having an opening extending therethrough. A first seal is provided within the interior chamber of the syringe barrel and a second seal is provided for sealing the opening of the distal end of the syringe barrel. The second seal is deformable upon a change in pressure within the interior chamber. An indicator is associated with the second seal and has a first distinguishing feature indicating an untampered state and a second distinguishing feature indicating a tampered state. The indicator is adapted for movement upon a change of pressure within the syringe barrel such that the second distinguishing feature is located in a viewable location. The syringe assembly can include a plunger assembly comprising a plunger head extending within the syringe barrel, wherein this plunger head forms the first seal within the interior chamber of the syringe barrel. Tampering of contents within the syringe barrel causes a change in pressure within the syringe barrel resulting in a deformation of the second seal and movement of the indicator to position the second distinguishing feature in the viewable location. A tip cap can be located about the second seal and the distal end of the syringe barrel. The tip cap can include a hollow portion and at least one viewing portion extending therethrough. The indicator is positioned within the hollow portion of the tip cap so that the first distinguishing feature is viewable through the viewing portion when the syringe assembly is in an untampered state, and the second distinguishing feature is viewable through the viewing portion when the syringe assembly is in a tampered state. The tip cap can include biased flexible fingers located in a sidewall thereof so that upon movement of the indicator showing a tampered state, the flexible fingers bias into the hollow portion of the tip cap to contact the indicator and prevent a return of the indicator to a pre-tampered position. The first distinguishing feature and the second distinguishing feature of the indicator can comprise a color change, an indicia change, or any other type of visually distinguishable contrast.

According to one embodiment, the interior chamber of the syringe can be pressurized to have a positive (above atmospheric) pressure such that tampering results in a reduction of the pressure within the syringe barrel which results in movement of the second seal toward the proximal end of the barrel. According to an alternative embodiment, the interior chamber of the syringe can be pressurized to have a negative (below atmospheric) pressure such that tampering results in an increase of pressure within the syringe barrel and a movement of the second seal in a forward or distal direction with respect to the syringe barrel and a bottom face of the tip cap.

According to yet another aspect, the invention is directed to a tamper evident pre-filled syringe assembly comprising a syringe barrel extending between a proximal end and a distal end, the distal end having an opening extending therethrough. The assembly further includes a plunger assembly comprising a plunger head extending within the syringe barrel at a position between the proximal end of the syringe barrel and the opening of the distal end forming an interior chamber therebetween, with the plunger head forming a first seal within the interior chamber. A second seal seals the interior chamber adjacent the opening of the distal end of the syringe barrel. The second seal is deformable upon a change in pressure within the interior chamber. An indicator is associated with the second seal, with the indicator adapted for movement upon deformation of the second seal. Tampering of the contents within the interior chamber causes a change in pressure within the interior chamber, resulting in a deformation of the second seal and movement of the indicator to provide a visual indication of tampering.

BRIEF DESCRIPTION OF THE DRAWINGS

FIG. 3B is a cross-sectional perspective view of the tip cap of FIG. 3A.

FIG. 3C is a cross-sectional side elevational view of the tip cap of FIG. 3A.

DESCRIPTION OF THE PREFERRED EMBODIMENTS

Figure 1:
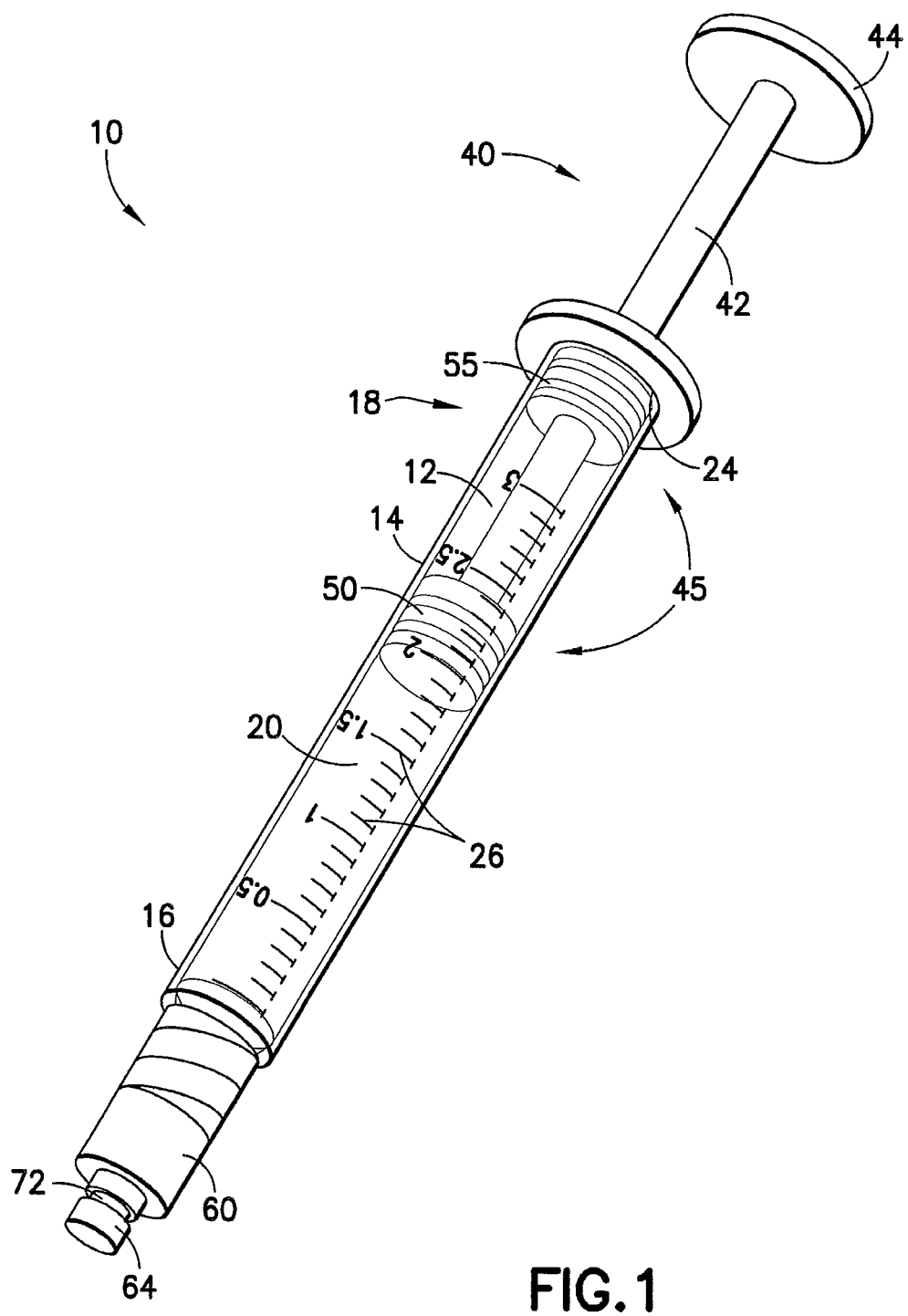
FIG. 1 is a perspective view of a pre-filled positive pressurized syringe including the tamper evident tip cap according to a first embodiment of the invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIGS. 1, 3B-3C, and 4B-4C, which depict a syringe assembly, generally indicated as 10, adapted for dispensing and delivery of a fluid. Syringe assembly 10 is intended for use for injection or infusion of fluid, such as a medication, directly into a patient, and is generally shown and described for purposes of the present description as a hypodermic syringe. Syringe assembly 10 is contemplated for use in connection with a needle such as by connecting syringe assembly 10 to a separate needle assembly (not shown), or alternatively for connection with a separate intravenous (IV) connection assembly (not shown).

The syringe assembly 10 includes a syringe barrel 12 defined by barrel wall 14 extending between a distal or forward end 16 and a proximal or rearward end 18, thereby defining an interior chamber 20 of the syringe barrel 12. The syringe barrel 12 may be in the general form of an elongated cylindrical barrel as is known in the art for the general shape of a hypodermic syringe, although other forms for containing a fluid for delivery are also contemplated by the present invention. Additionally, the syringe barrel 12 may be formed of glass, or may be injection molded from thermoplastic material such as polypropylene and polyethylene according to techniques known to those of ordinary skill in the art, though it is to be appreciated that the syringe barrel 12 may be made from other suitable materials and according to other applicable techniques.

Figure 2:
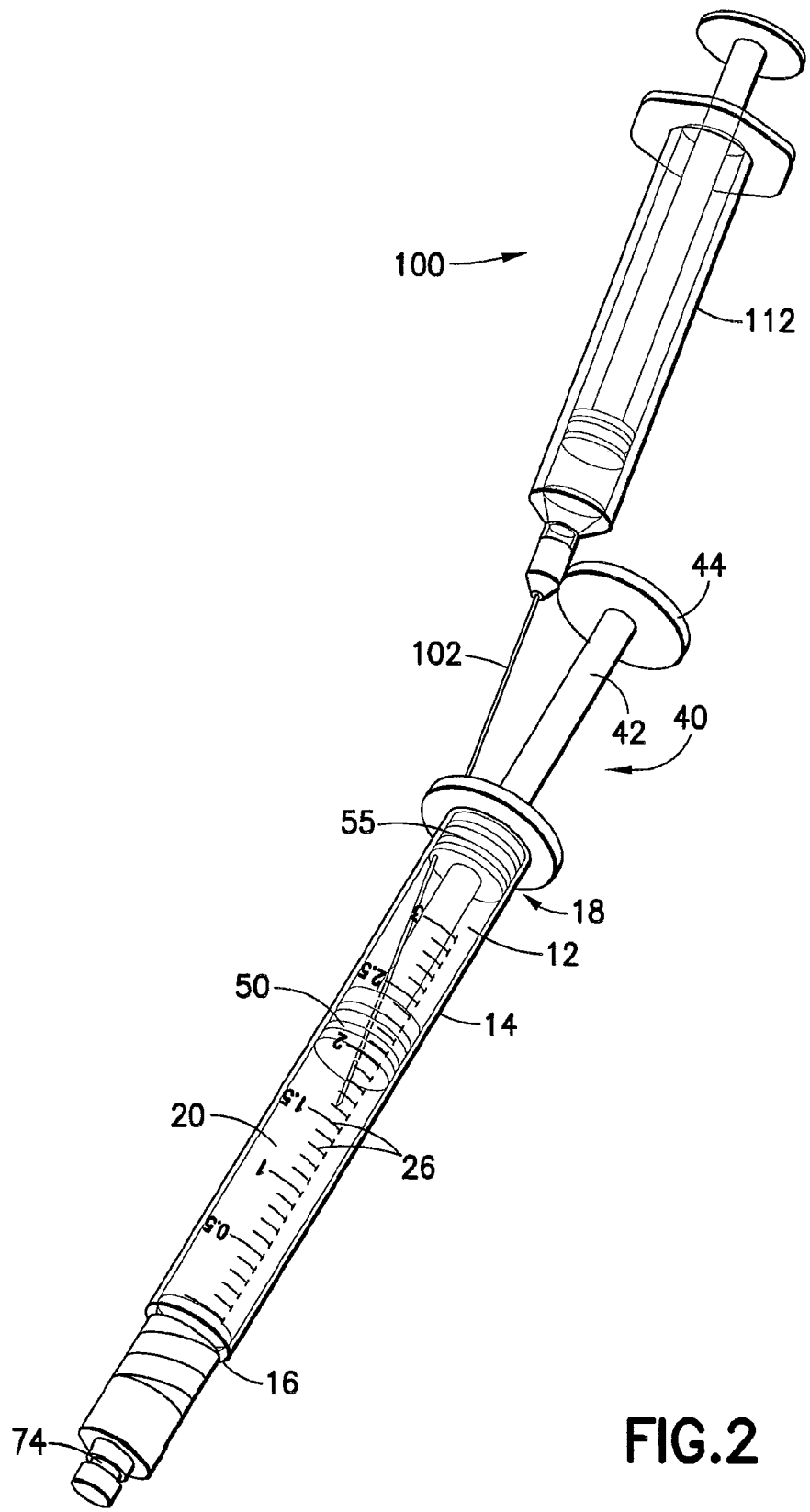
FIG. 2 is a perspective view of a pre-filled syringe showing tampering of the syringe contents.
Figure 3A:
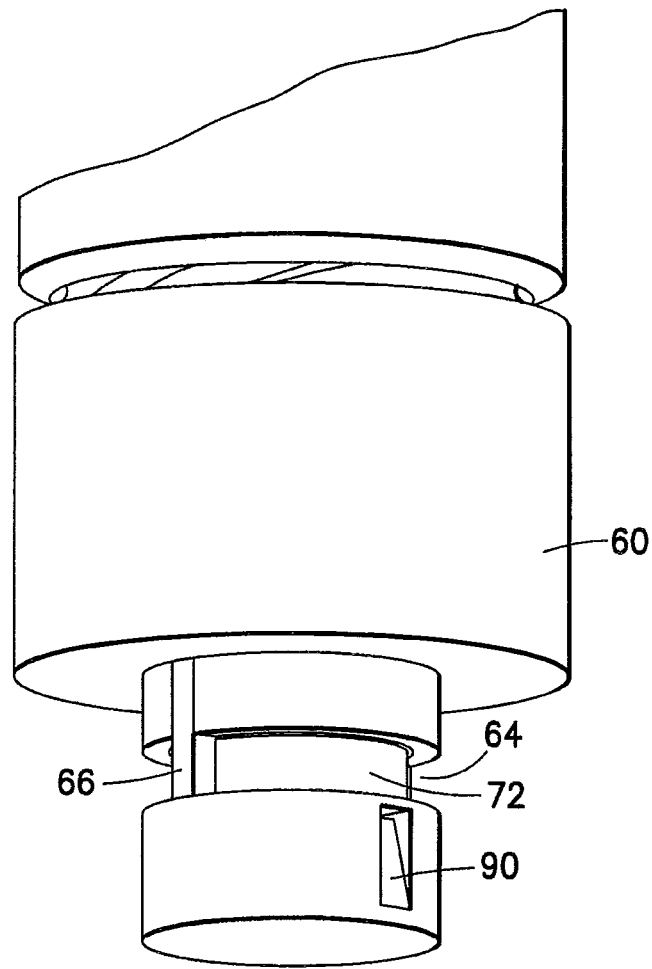
FIG. 3A is a perspective view of the tip cap of the invention prior to tampering.
Figure 4A:
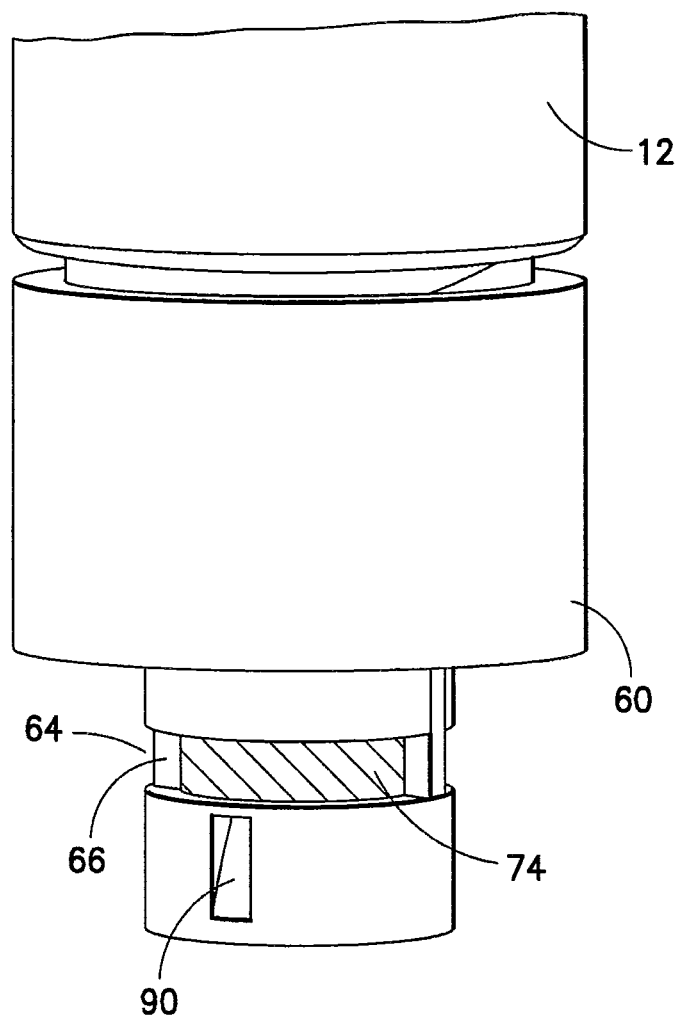
FIG. 4A is a perspective view of the tip cap of the invention after tampering.
Figure 4C:
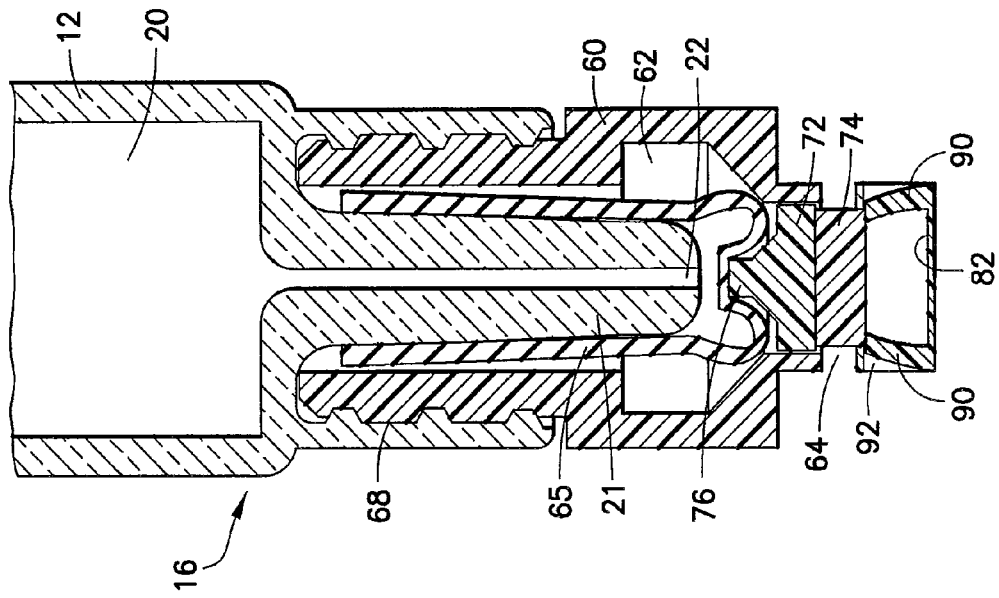
FIG. 4C is a cross-sectional side elevational view of the tip cap of FIG. 4A.
Figure 4B:
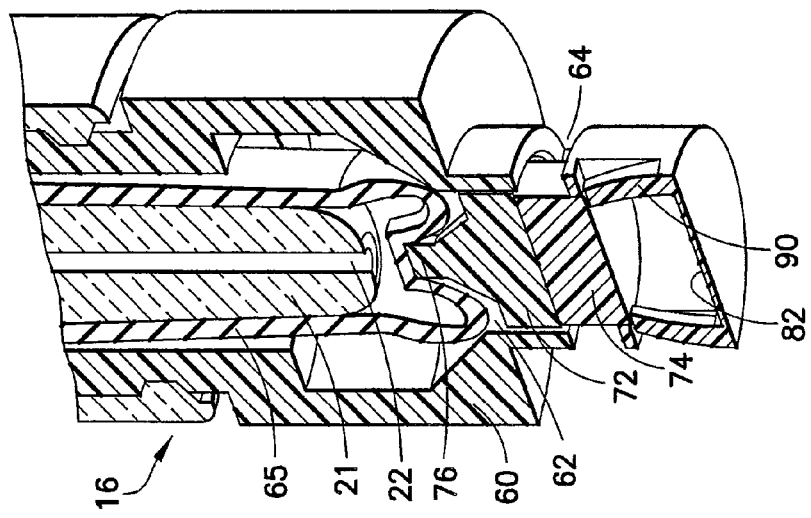
FIG. 4B is a cross-sectional perspective view of the tip cap of FIG. 4A.

As illustrated in FIGS. 3B-3C and 4B-4C, the distal end 16 of the syringe barrel 12 terminates in a tip 21 having an outlet opening 22. As shown in FIGS. 1-2, the proximal end 18 is generally open-ended at rearward opening 24, but is intended to be closed off to the external environment, as will be discussed in more detail herein.

The syringe barrel 12 may include markings, such as graduations 26 on the wall 14 thereof, for providing an indication as to the level or amount of fluid contained within the syringe barrel 12. Such markings may be provided on the external wall, the internal wall, or integrally formed or otherwise within the wall of syringe barrel 12. Alternatively, or in addition thereto, the markings may provide a description of the contents of the syringe, or other identifying information, as may be known in the art.

As noted, distal end 16 of syringe barrel 12 includes an outlet opening 22. The profile of outlet opening 22 may be adapted for engagement with a separate dispensing device, such as a needle assembly or IV connection assembly, and therefore may include a mechanism for such engagement, for example, a generally tapered luer tip, for engagement with a separate tapered luer mating surface (not shown) of such a separate device for attachment therewith. In addition, a mechanism for locking engagement therebetween may also be provided, such as a luer collar or luer lock including interior threads. Such luer connections and luer locking mechanisms are well known in the art.

Referring back to FIGS. 1-2, the syringe assembly 10 further includes a plunger assembly, generally indicated as 40, a portion of which is adapted to be disposed at least partially within the syringe barrel 12. Plunger assembly 40 provides a mechanism for dispensing fluid contained within the interior chamber 20 of syringe barrel 12. In particular, plunger assembly 40 includes a plunger rod 42, which provides a mechanism for extension of a stopper portion such as plunger head 50 disposed within interior chamber 20 for dispensing the contents of the syringe assembly upon the application of a distal force to thumb press 44 located at one end of the plunger rod 42.

All of the components of syringe assembly 10 may be constructed of any known material, and are desirably constructed of medical grade polymers.

As stated above, the syringe assembly 10 is particularly useful as a pre-filled syringe, and therefore may be provided for end use with a fluid, such as a medication, contained within interior chamber 20 of syringe barrel 12, pre-filled by the manufacturer. In this manner, syringe assembly 10 can be manufactured, pre-filled with a medication, sterilized, and packaged in appropriate packaging for delivery, storage, and use by the end user, without the need for the end user to fill the syringe with medication from a separate vial prior to use.

As previously discussed, steps have been taken to ensure the integrity of the contents of the syringe assembly 10, such as through the use of snap caps and shrink wrap bands, however, tampering with and/or theft of the contents can still occur. Reference is made to FIG. 2 which shows one technique for stealing the contents within the syringe assembly 10 wherein a separate syringe assembly, generally indicated as 100 and including a needle 102, is used to pierce the plunger head 50 and withdraw the pre-filled contents or medication from within the interior chamber 20 into a barrel 112 of the separate syringe assembly 100. Then, a saline solution or even water can be injected into the syringe barrel 12 of the pre-filled syringe assembly 10, via another syringe assembly (not shown) piercing the plunger head 50 a second time such that the same content volume is maintained in the pre-filled syringe and it appears that the contents or medication within the syringe assembly 10 is intact or unaltered.

Figure 5:
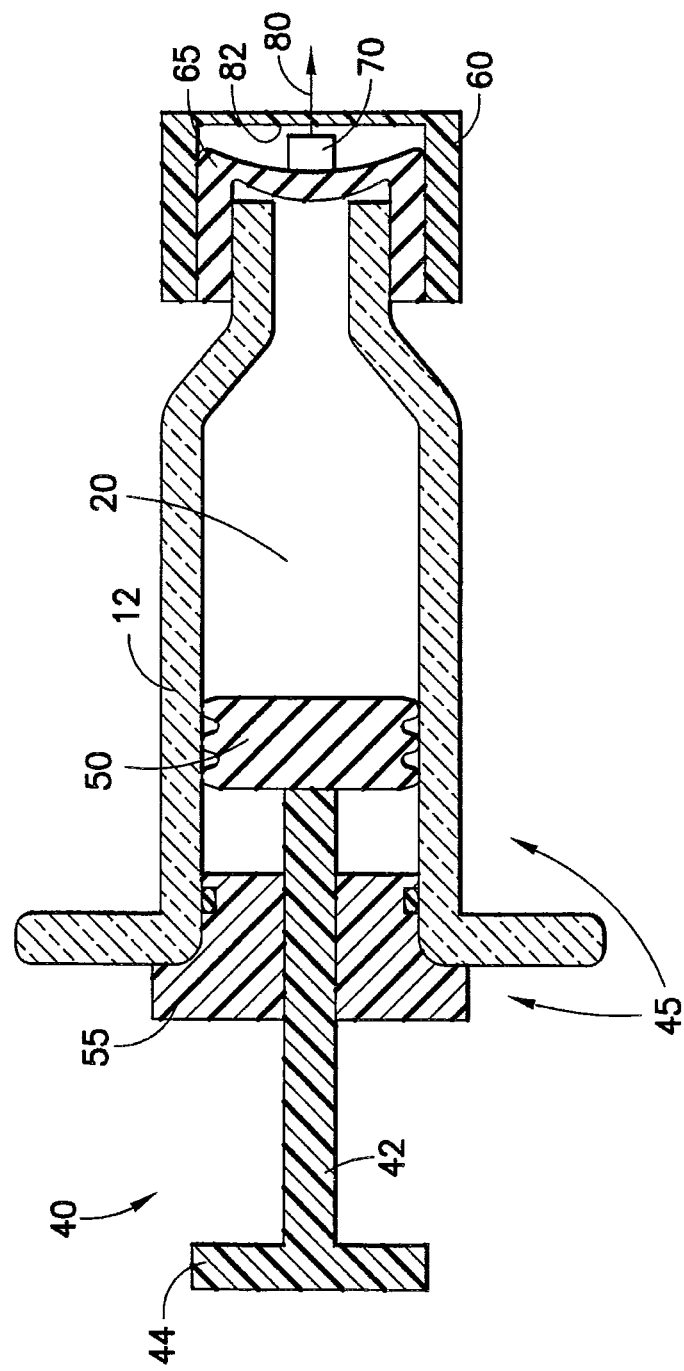
FIG. 5 is a side elevational view of a pre-filled vacuum pressurized syringe including the tamper evident tip cap according to a second embodiment of the invention.

With continuing reference to FIGS. 1, 3A-3B, 4A-4C, and 5, the present invention utilizes a pre-filled syringe assembly 10 wherein the syringe barrel defines a pressure contained within the interior chamber. This pressure can be a positive pressure, a negative pressure, or even an ambient pressure. A tamper evident tip cap 60 adapted to change state upon a change in pressure within the interior chamber 20 is provided to indicate whether or not a change in pressure within the interior chamber has occurred and if the contents of the syringe assembly 10 have been compromised. In particular, the syringe assembly 10 includes a first seal for providing an air-tight and fluid-tight environment within the interior chamber 20 to prevent escape of air/fluid from escaping through the rearward opening 24 at the proximal end of the syringe barrel 12. As shown in FIGS. 1 and 5, this first seal can comprise the plunger head 50, in which case the plunger head 50 is constructed of suitable material for achieving an air-tight and fluid-tight seal of the interior of interior chamber 20. In embodiments where the plunger head 50 does not provide for an air-tight and fluid-tight seal, or when a secondary or additional seal is desired, a separate sealing member 55 may be provided proximate to plunger head 50, such as sealing member 55 shown in FIGS. 1 and 5 enclosing the opening within proximal end 18 of syringe barrel 12. In this manner, plunger head 50 and sealing member 55 may act together to provide a first seal, generally indicated as 45 in FIGS. 1 and 5.

A second seal 65 as shown in FIGS. 3B-3C, 4B-4C, and 5 is positioned about the distal end 16 of the syringe barrel 12 for sealing the outlet opening 22 extending through the tip 21. This second seal 65 may be formed of a flexible deformable material and the first and second seals provide a sealing of the syringe barrel 12 so as to maintain a predetermined pressure therein within the interior chamber 20.

The tip cap 60 is located about the second seal 65 and the distal end 16 of the syringe barrel 12. This tip cap 60 includes a hollow portion 62 and at least one viewing portion or window 64 extending therethrough. This viewing portion 64 can be a cut-out portion in the wall 66 of the tip cap 60 or a transparent portion of the tip cap 60. The tip cap 60 can be secured to the distal end 16 of the syringe barrel 12 by a threaded engagement 68 or any other well known means.

An indicator 70 capable of visually changing state upon a change in pressure within the syringe barrel 12 is located within the hollow portion 62. According to one embodiment, the indicator 70 can have at least a first distinguishing feature 72 and a second distinguishing feature 74. The first distinguishing feature 72 can represent the syringe assembly as being in an untampered state. The second distinguishing feature 74 can represent the syringe assembly as being in a tampered state. The indicator 70 has a portion 76 positioned in contact with the second seal 65 such that at least a portion of the first distinguishing feature 72 is viewable through the viewing portion 64 of the tip cap 60. Any tampering of the contents within the syringe barrel 12 will cause a change in pressure within the syringe barrel 12 resulting in a deformation of the second seal 65. As particularly shown in FIGS. 4B and 4C, the interior chamber 20 can be positively pressurized such that a change or reduction in pressure results in a deformation of the second seal 65 of the syringe assembly 10 and causes movement of the indicator 70, such as toward the proximal end 18 of the syringe barrel 12, so that at least a portion of the second distinguishing feature 74 is viewable through the viewing portion 64 indicating tampering of the syringe contents. This would alert the clinician that the medication should not be administered. The first and second distinguishing features 72, 74 of the indicator 70 can include differing colors, such as "green" for an untampered state and "red" showing a tampered state; words, such as "go" and "stop"; or any other type of indicia indicating the state of the syringe contents. Alternatively, the first and second distinguishing features 72, 74 can include any other visually identifiable contrast, to alert a medical practitioner of the status of the contents of the syringe.

According to a second embodiment, as shown in FIG. 5, the pressurized syringe assembly 10 can be negatively pressurized via a vacuum (below atmospheric) pressure such that tampering results in an increase of pressure within the syringe barrel 12 which results in movement of the second seal 65 in a forward or distal direction 80 with respect to the syringe barrel 12 and a bottom face 82 of the tip cap 60. This forward movement of the second seal 65 can result in movement of the indicator 70 showing that tampering of the syringe contents has occurred.

Since the interior chamber 20 of the syringe barrel 12 is sealed via first seal 45 and second seal 65, any tampering with the syringe contents would result in a change in pressure within the chamber, which would cause deformation of the second seal 65 and movement of the indicator 70. Accordingly, although embodiments showing a positively pressurized or a negatively pressurized chamber within the syringe barrel are specifically described and shown in the drawings, it can be appreciated that the syringe barrel of the pre-filled syringe assembly can define any pressure within the interior chamber 20, such as atmospheric or ambient pressure, so long as the deformation of seal 65 is achieved through a change in pressure across seal 65 as a pressure gradient, based on a change in pressure within interior chamber 20.

A holding member can be provided for preventing the indicator from returning to an original pre-tampered state. One example of a holding member can be flexible fingers 90, as shown in FIGS. 3A-3C and 4A-4C which are located within the hollow portion 62 of the tip cap 60 to prevent movement of the indicator to a pre-tampered position once tampering has occurred. In particular, these flexible fingers 90 can extend upwardly with respect to the bottom face 82 of tip cap 60. These flexible fingers 90 can be normally biased in an outward direction with respect to a bottom wall portion 92 of the tip cap 60. Upon movement of the indicator 70 in an upward direction or toward the proximal end 18 of the syringe barrel 12, these fingers 90 flex inward and below the indicator 70, holding the indicator in place such that the second distinguishing feature 74 is positioned within the viewing portion or window 64. The inward biasing of the flexible fingers 90 can not be reversed, thus preventing undetected tampering of the contents of the syringe assembly 10. In accordance with an additional embodiment, the flexible fingers 90 may be integral with the indicator 70 such that as the indicator 70 is displaced, the flexible fingers 90 lock into the tip cap 60 to prevent reversal of movement. In accordance with another embodiment, a washer (not shown), such as a steel washer, may be attached to the indicator 70 to further prevent reversal of motion. In this configuration, as the indicator 70 moves in a proximal direction, portions of the washer, such as points thereon, drag along the interior diameter of the tip cap 60. If pressure inside the syringe is increased to move the indicator 70 in a distal direction, the washer flexes and increases in diameter thereby preventing distal movement.

While the above description is directed to the prevention of tampering and/or theft of the syringe contents, it can be appreciated that the present invention can also be used to detect leakage of the contents in positively pressurized syringe assemblies and to detect the entrance of unwanted contaminants within negatively pressurized syringe assemblies.

In accordance with an embodiment of the present invention, if the syringe is pressurized, then the plunger rod assembly may be biased to move proximally. The clinician may, upon removing the syringe assembly from the packaging, apply a twist to the plunger rod, disengaging the retaining features between the plunger rod and the barrel that maintain the pressure. The assembly will then be displaced proximally by the pressure inside the syringe and a color change, molded or affixed to the plunger rod, could appear to indicate that the internal pressure has been held up to the point of disengagement by the clinician. In certain embodiments, this color change may be evident as the device is held within the clinician's hand.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

The invention claimed is:

1. A tamper evident pre-filled syringe assembly comprising:
 a syringe barrel defining an interior chamber, a proximal end, and a distal end terminating in a tip having an opening extending therethrough, said syringe barrel defining a pressure contained within said interior chamber;
 at least one seal associated with the syringe assembly; and
 an indicator separate and distinct from and in contact with the at least one seal, said indicator configured for changing state upon movement of the at least one seal caused by a change in the pressure within the interior chamber to indicate tampering of contents within the syringe assembly.

2. The syringe assembly of claim 1 wherein the at least one seal comprises a first seal for sealing the interior chamber and a second seal for sealing the opening, the second seal extending through the tip of the distal end of the syringe barrel.

3. The syringe assembly of claim 2, further comprising a plunger assembly including a plunger head extending within the syringe barrel, wherein the plunger head comprises the first seal.

4. The syringe assembly of claim 2 wherein the second seal is positioned about the distal end of the syringe barrel and is formed from a deformable material and wherein tampering of contents within the interior chamber causes a change in the pressure within the interior chamber resulting in a deformation of the second seal.

5. The syringe assembly of claim 4 wherein the indicator is associated with the second seal and wherein deformation of the second seal results in movement of the indicator.

6. The syringe assembly of claim 5 wherein the pressure defined by the interior chamber is a positive pressure and wherein tampering with the syringe contents reduces the pressure within the interior chamber resulting in deformation of the second seal and movement of the indicator toward a proximal end of the syringe assembly.

7. The syringe assembly of claim 5 wherein the pressure defined by the interior chamber is a negative pressure and wherein tampering with the syringe contents increases the pressure within the interior chamber resulting in deformation of the second seal and movement of the indicator toward a distal end of the syringe assembly.

8. The syringe assembly of claim 1 wherein the change in state of the indicator comprises a visual change.

9. The syringe assembly of claim 8 wherein the visual change is a color change, an indicia change, or any visually distinguishable contrast.

10. The syringe assembly of claim 1 including a tip cap located about the distal end of the syringe barrel, said tip cap containing at least a portion of said indicator therein and at least one viewing portion for viewing the change of state of said indicator.

11. The syringe assembly of claim 10 wherein the viewing portion comprises a cut-out portion in a wall of the tip cap.

12. The syringe assembly of claim 10 wherein the viewing portion comprises a transparent portion in the tip cap.

13. The syringe assembly of claim 10 wherein the tip cap is threadedly engaged with the distal end of the syringe barrel.

14. The syringe assembly of claim 1 including a holding member for cooperating with the indicator and for preventing the indicator from returning to an original pre-tampered state.

15. The syringe assembly of claim 14 wherein the holding member comprises flexible fingers or a washer.

16. A tamper evident pre-filled syringe assembly comprising:
a syringe barrel defining an interior chamber, a proximal end, and a distal end having an opening extending therethrough;
a first seal within the interior chamber of the syringe barrel;
a second seal sealing the opening of the distal end of the syringe barrel, said second seal being deformable upon a change in pressure within the interior chamber; and
an indicator separate and distinct from and associated with the second seal and having a first distinguishing feature indicating an untampered state and a second distinguishing feature indicating a tampered state,
wherein the indicator is adapted for movement upon deformation of the second seal caused by a change of pressure within the interior chamber such that the second distinguishing feature is located in a viewable location.

17. The syringe assembly of claim 16, further comprising a plunger assembly comprising a plunger head extending within the syringe barrel, the plunger head forming said first seal within the interior chamber of the syringe barrel.

18. The syringe assembly of claim 16 wherein tampering of contents within the syringe barrel causes the change in pressure within the interior chamber resulting in the deformation of the second seal and movement of the indicator to position the second distinguishing feature in the viewable location.

19. The syringe assembly of claim 16 including a tip cap located about the second seal and the distal end of the syringe barrel, said tip cap including a hollow portion and at least one viewing portion extending therethrough.

20. The syringe assembly of claim 19 wherein the indicator is positioned within the hollow portion of the tip cap and wherein the first distinguishing feature is viewable through the viewing portion when the syringe assembly is in an untampered state and the second distinguishing feature is viewable through the viewing portion when the syringe assembly is in a tampered state.

21. The syringe assembly of claim 20 including biased flexible fingers located in a sidewall of the tip cap and wherein upon movement of the indicator showing a tampered state, said flexible fingers bias into the hollow portion of the tip cap to contact the indicator and prevent a return of the indicator to a pre-tampered position.

22. The syringe assembly of claim 16 wherein the first distinguishing feature and the second distinguishing feature of the indicator comprise a color change, an indicia change, or any visually distinguishable contrast.

23. A tamper evident pre-filled syringe assembly comprising:
a syringe barrel extending between a proximal end and a distal end, the distal end having an opening extending therethrough;
a plunger assembly comprising a plunger head extending within the syringe barrel at a position between the proximal end of the syringe barrel and the opening of the distal end forming an interior chamber therebetween, the plunger head forming a first seal within the interior chamber;
a second seal sealing the interior chamber adjacent the opening of the distal end of the syringe barrel, said second seal being deformable upon a change in pressure within the interior chamber; and
an indicator separate and distinct from and associated with the second seal, the indicator adapted for movement upon deformation of the second seal,
wherein tampering of contents within the interior chamber causes a change in pressure within the interior chamber resulting in a deformation of the second seal and movement of the indicator to provide a visual indication of tampering.

24. The syringe assembly of claim 23 wherein the indicator is a separate member from the second seal.

25. A tamper evident pre-filled syringe assembly comprising:
a syringe barrel defining an interior chamber, a proximal end, and a distal end terminating in a tip having an opening extending therethrough, said syringe barrel defining a pressure contained within said interior chamber;
at least one seal associated with the syringe assembly;
an indicator in contact with the at least one seal, said indicator configured for changing state upon movement of the at least one seal caused by a change in the pressure within the interior chamber to indicate tampering of contents within the syringe assembly; and
a tip cap located about the distal end of the syringe barrel, said tip cap containing at least a portion of said indicator therein and at least one viewing portion for viewing the change of state of said indicator.

* * * * *